(12) United States Patent  
Maity et al.

(10) Patent No.: US 9,759,610 B2  
(45) Date of Patent: *Sep. 12, 2017

(54) METHOD AND DEVICE FOR DISSOLVED GAS ANALYSIS

(71) Applicant: General Electric Company, Schenectady, NY (US)

(72) Inventors: Sandip Maity, Bangalore (IN); Nagapriya Kavoori Sethumadhavan, Bangalore (IN); Shashank Sinha, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 285 days.

This patent is subject to a terminal disclaimer.

(21) Appl. No.: 13/950,733

(22) Filed: Jul. 25, 2013

(65) Prior Publication Data

US 2014/0036954 A1    Feb. 6, 2014

(30) Foreign Application Priority Data

Aug. 1, 2012    (IN) .......................... 3163/CHE/2012

(51) Int. Cl.
G01J 5/00 (2006.01)
G01N 21/3504 (2014.01)
G01N 25/48 (2006.01)
G01N 21/359 (2014.01)

(52) U.S. Cl.
CPC ........ G01J 5/0014 (2013.01); G01N 21/3504 (2013.01); G01N 21/359 (2013.01); G01N 25/4873 (2013.01)

(58) Field of Classification Search
CPC .............. G01J 5/0014; G01N 21/3504; G01N 25/4873; G01N 21/359

USPC ......................................................... 73/53.01
See application file for complete search history.

(56) References Cited

U.S. PATENT DOCUMENTS

| 2,790,081 A * | 4/1957 | Munday ............. G01N 21/3504 136/215 |
| 4,928,015 A * | 5/1990 | Butler ..................... G01J 3/453 250/339.08 |
| 5,225,334 A * | 7/1993 | Tanno ..................... C12Q 1/06 374/45 |

(Continued)

FOREIGN PATENT DOCUMENTS

| JP | 2006267047 A2 | 10/2006 |
| WO | 2007136593 A2 | 11/2007 |
| WO | WO 2008103837 A1 * | 8/2008 ......... G01N 33/2841 |

OTHER PUBLICATIONS

Yun et. al.: "Acetylene detection by laser resonant photoacoustic spectrometry", Gaodianya Jishu/High Voltage Engineering, Sep. 30 2009; pp. 2156-2162. ISSN: 10036520.

(Continued)

*Primary Examiner* — Marrit Eyassu
(74) *Attorney, Agent, or Firm* — GE Global Patent Operation; Scott R. Stanley (57) ABSTRACT

A method for dissolved gas analysis is presented. The method includes the steps of irradiating a fluid with electromagnetic radiation; and determining a concentration of a gas as a function of a temperature change of the fluid in response to the irradiation. A device for such an analysis of dissolved gases in a fluid, and a system having such device are also described.

15 Claims, 6 Drawing Sheets

(56) References Cited

U.S. PATENT DOCUMENTS

| | | | | |
|---|---|---|---|---|
| 5,272,090 | A * | 12/1993 | Gavish | G01N 21/643 356/402 |
| 5,824,885 | A * | 10/1998 | Lekholm | A61M 16/209 128/203.12 |
| 5,852,308 | A * | 12/1998 | Wood | G01N 21/171 250/343 |
| 6,121,627 | A * | 9/2000 | Tulip | G01N 21/39 250/343 |
| 6,138,497 | A * | 10/2000 | Nix | G01N 7/14 250/339.13 |
| 6,202,480 | B1 * | 3/2001 | Mauze | G01N 25/64 374/109 |
| 8,154,731 | B2 | 4/2012 | Arnvidarson et al. | |
| 2004/0113070 | A1 * | 6/2004 | Nichols | G01N 21/8422 250/302 |
| 2006/0139646 | A1 * | 6/2006 | DiFoggio | E21B 49/10 356/436 |
| 2006/0188398 | A1 * | 8/2006 | Yano | B82Y 20/00 422/82.01 |
| 2010/0006284 | A1 * | 1/2010 | Sonne | E21B 47/10 166/264 |
| 2010/0159610 | A1 * | 6/2010 | Sun | G01N 21/78 436/147 |
| 2011/0153223 | A1 * | 6/2011 | Gentala | G01N 21/3504 702/24 |
| 2011/0317164 | A1 * | 12/2011 | Cole | G01N 21/031 356/437 |

OTHER PUBLICATIONS

Yun et. al.: "New photoacoustic detection method for acetylene dissolved in transformer oil", 2011 Asia-Pacific Power and Energy Engineering Conference, 2011 Article No. 5748712.

Yun et. al.: "Photoacoustic Detection of Methane Dissolved in Transformer Oil", Zhongguo Dianji Gongcheng Xuebao (Proceedings of the Chinese Society of Electrical Engineering), Dec. 5, 2008.

European Search Report and Written Opinion issued in connection with corresponding EP Application No. 13178577.6-1554 on Oct. 31, 2013.

Rosengren, "An opto-thermal gas concentration detector", Infrared Physics, vol. No. 13, Issue No. 3, pp. 173-182, Aug. 1, 1973.

Yun et al., "Infrared absorption properties analysis of dissolved gases in transformer oil", 2010 International Conference on Power System Technology, pp. 1-6, Oct. 1, 2010.

* cited by examiner

METHOD AND DEVICE FOR DISSOLVED GAS ANALYSIS

BACKGROUND OF THE INVENTION

Technical Field

The subject matter disclosed generally relates to measuring and testing of dissolved gases, and more specifically to a method and apparatus for selectively detecting and monitoring dissolved gases in a fluid, such as transformer oil.

Related Art

Electrical equipment, particularly medium-voltage or high-voltage electrical distribution equipment, requires a high degree of electrical and thermal insulation between components. Accordingly, it is well known to encapsulate components of electrical equipment, such as coils of a transformer, in a containment vessel and to fill the containment vessel with a fluid. The fluid facilitates dissipation of heat generated by the components and can be circulated through a heat exchanger to efficiently lower the operating temperature of the components. The fluid also serves as electrical insulation between components or to supplement other forms of insulation disposed around the components, such as cellulose paper or other insulating materials. Any fluid having the desired electrical and thermal properties can be used. However, electrical equipment is typically filled with various oils, such as castor oil, mineral oil, and/or a synthetic "oil" such as chlorinated diphenyl or silicone oil.

Often electrical distribution equipment is used in a mission critical environment in which failure can be very expensive or even catastrophic because of a loss of electric power to critical systems. Also, failure of electrical distribution equipment ordinarily results in a great deal of damage to the equipment itself and surrounding equipment thus requiring replacement of expensive equipment. Further, such failure can cause injury to personnel due electric shock, fire, or explosion. Therefore, it is desirable to monitor the status of electrical equipment to predict potential failure of the equipment through detection of incipient faults and to take remedial action through repair, replacement, or adjustment of operating conditions of the equipment.

A known method of monitoring the status of fluid-filled electrical equipment is to monitor various parameters of the fluid. For example, the temperature of the fluid and the total combustible gas (TCG) in the fluid is known to be indicative of the operating state of fluid-filled electrical equipment. Therefore, monitoring these parameters of the fluid can provide an indication of any incipient faults in the equipment. For example, it has been found that carbon monoxide and carbon dioxide increase in concentration with thermal aging and degradation of cellulosic insulation in electrical equipment. Hydrogen and various hydrocarbons (such as acetylene and ethylene, and their derivatives) increase in concentration due to hot spots caused by circulating currents and dielectric breakdown such as corona or arcing. Concentrations of oxygen and nitrogen indicate the quality of the gas pressurizing system employed in large equipment, such as transformers. Accordingly "dissolved gas analysis" (DGA) has become a well-accepted method of discerning incipient faults in fluid-filled electric equipment.

Generally, an amount of fluid is removed from the containment vessel of the equipment through a valve. The removed fluid is then subjected to testing for dissolved gas in a lab or by equipment in the field. This method of testing is referred to herein as "off-line" DGA. Since the gases are generated by various known faults, such as degradation of insulation material or other portions of electric components in the equipment, turn-to-turn discharges in coils, overloading, loose connections, or the like, various diagnostic theories have been developed for correlating the quantities of various gases in fluid with particular faults in electrical equipment in which the fluid is contained.

Known methods of off-line DGA typically require extraction of gases from the fluid for several quantitative analyses. These extracted gases are often analyzed by using photoacoustic spectroscopy or gas chromatography. The gas concentration in the fluid is generally calculated from the measured concentrations of the extracted gases. However, these methods suffer from inaccuracy, uncertainties and repeatability issues generally involved with the complicated extraction process. In addition to this, the gas concentration in liquid is calculated from the measured concentrations of the extracted gases. The calculations have several assumptions involved, leading to errors and uncertainties.

BRIEF DESCRIPTION OF THE DISCLOSED EMBODIMENTS

These and other drawbacks associated with such conventional approaches are addressed here by providing, in various embodiments, a method including the steps of irradiating a fluid with electromagnetic radiation having a wavelength corresponding to a spectral absorption range of a gas in the fluid; and determining a concentration of the gas based on a temperature change of the fluid in response to the irradiation. For example, the irradiating step may include irradiating the fluid with radiation from a laser source.

Also disclosed is a device including a fluid container; an electromagnetic radiation source disposed for directing radiation into the fluid container; a temperature sensor for monitoring a temperature of the fluid contained in the fluid container; and a data analyzer for determining concentration of a gas in the fluid based on a temperature change of the fluid in response to radiation from radiation source.

In one embodiment, a system includes the device in fluid communication with a transformer to analyze dissolved gases in the transformer oil.

DRAWINGS

These and other features, aspects, and advantages of the present invention will become better understood when the following detailed description is read with reference to the accompanying drawings, wherein.

DETAILED DESCRIPTION

The invention includes embodiments that relate to a method and a device for measuring and testing dissolved gases in a fluid, for example transformer oil or cooling fluid. As discussed in detail below, some of the embodiments of the present invention provide a method for selectively detecting and monitoring dissolved gases in a fluid by using calorimetry, and a device for the same. These embodiments advantageously provide a useful method for measuring the composition and concentration of the dissolved gases without necessarily extracting gases from the fluid.

Though the present discussion provides examples in the context of an insulating fluid used in electric power industry, typically in transformers, these processes can be applied to any other fluid or application. In some embodiments, the insulating fluid may include a dielectric or insulating oil, a mineral oil, a coolant, or the like. The method and device described herein may be used with other industries such as chemical industry, petroleum industry, food industry, and water industry. Other suitable examples of the fluid may include vegetable oils, beverages, chemical compounds, or the like.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. As used herein, the term "and/or" includes any and all combinations of one or more of the associated listed items.

Approximating language, as used herein throughout the specification and claims, may be applied to modify any quantitative representation that could permissibly vary without resulting in a change in the basic function to which it may be about related. Accordingly, a value modified by a term such as "about" is not limited to the precise value specified. In some instances, the approximating language may correspond to the precision of an instrument for measuring the value.

Some embodiments of the invention provide a method for detecting and monitoring a selected gas in a fluid using calorimetry. The method involves the steps of irradiating a fluid with electromagnetic radiation; and determining a concentration of a gas in the fluid as a function of the temperature change of the fluid in response to the irradiation. The fluid is irradiated with a radiation having a wavelength or wavelengths corresponding to a spectral absorption range of a selected gas or gases.

In some embodiments, the fluid is substantially transparent to the radiation of a particular wavelength. The fluid may absorb a small amount of the radiation or substantially no radiation. In these instances, when the fluid is irradiated with the radiation at a particular wavelength, the radiation may or may not be absorbed depending on the presence or absence of a selected gas in the fluid. In presence of a gas, the radiation of a particular wavelength corresponding to the spectral absorption range of the gas is absorbed by the gas. On absorption of the radiation energy, the temperature of the gas increases and subsequently heat is transferred between the gas and surrounding fluid. The change in temperature of the fluid is a direct indication of the composition of the gas, and the magnitude of the change may be used to calculate the concentration of the gas in the fluid. No change in temperature on irradiation of the fluid by the radiation indicates absence of the selected gas in the fluid.

In some other embodiments, the fluid may absorb a substantial or partial amount of radiation of a particular wavelength. In such instances, the change in temperature of the fluid is measured relative to a change in temperature of a reference fluid in response to radiation of the same wavelength. The reference fluid does not contain any gas, or contains a known quantity of a gas. In these instances, when the fluid is irradiated with the radiation at a particular wavelength, the radiation is absorbed by the fluid as well as by a selected gas in the fluid if present. In other words, in presence of the gas, the absolute temperature change ($\Delta T_F$) of the fluid includes a change in temperature of the fluid in response to the radiation absorbed by the fluid and the gas. One skilled in the art acquainted with the details presented herein will appreciate that comparing this absolute change in temperature ($\Delta T_F$) of the fluid with a change in the temperature of the reference fluid ($\Delta T_{RF}$) may provide the change in temperature attributable to absorption of radiation by the gas. The difference in the temperature changes between the reference fluid and the fluid, that is ($\Delta T_F - \Delta T_{RF}$) may be a measure of the gas concentration in the fluid. In some other instances, the change in temperature of the fluid with respect to the change in the temperature of the reference fluid ($\Delta T_F - \Delta T_{RF}$) may be very small or none in absence of the selected gas.

Figure 1:
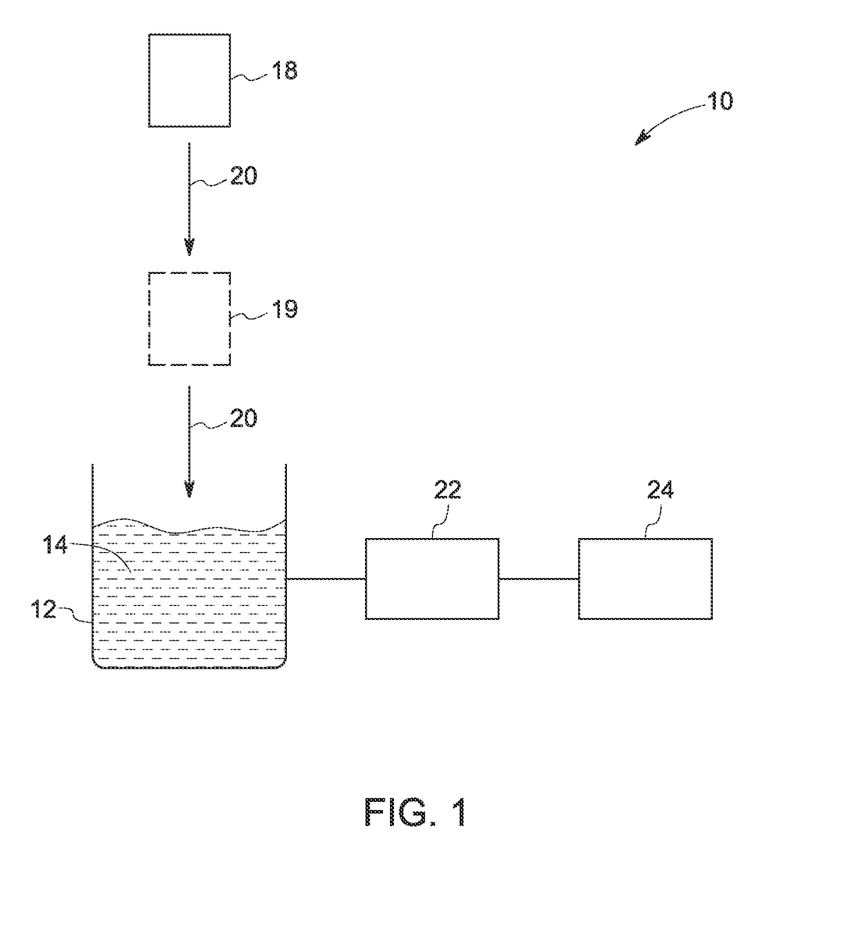
FIG. 1 is a schematic view of a device, in accordance with an embodiment of the invention.

A schematic of a device 10 for the detection and monitoring dissolved gases in a fluid is illustrated in FIG. 1. The device 10 includes a fluid container 12 to contain a fluid 14 to be analyzed. The container 12 may be of any shape having a volume to contain a sufficient amount of the fluid to be analyzed. The volume of the container 12 may be as small as 1 microliter. In some instances, the volume of the container 12 may be in a range from about 1 microliter to about 10 milliliters. In some specific instances, the volume may vary from about 5 microliters to about 5 milliliters. In some specific embodiments, the container 12 is cylindrical in shape with a cross section area. The cross section area may be circular, polygonal, or elliptical in shape.

The device 10 includes an electromagnetic radiation source 18. The radiation source 18 is disposed at such a position to direct radiation 20 into the fluid container 12. In some instances, a suitable optical arrangement 19 may be used to direct radiation 20 into the fluid container. For example, the radiation may be collected by an aspheric lens and collimated using a lens.

The radiation source produces radiation 20 at a wavelength or wavelengths corresponding to a spectral absorption range of a selected gas to be monitored in the fluid 14. Typically, a fluid may contain several dissolved gases. In one embodiment, the gas may include fault gases. As used herein, "fault gases" refers to gases liberated within equipment upon a fault in the equipment. For example, insulating materials within transformers and related equipment break down to liberate gases. The type and distribution of gases can be related to the type of electrical fault, and the rate of gas generation can indicate the severity of the fault. Examples of the fault gases dissolved in the dielectric oil, generally used in transformers, may include one or more dissolved gases such as hydrogen, oxygen, carbon monoxide, carbon dioxide, methane, ethane, ethylene, acetylene, and possibly other species.

To detect and monitor individual gas, particular wavelength or wavelengths corresponding to each gas may be directed to the fluid for selective detection of a gas in the fluid. For example, $C_2H_2$ has its fundamental absorption band between about 3200 cm$^{-1}$ to about 3350 cm$^{-1}$, and $CO_2$ has an absorption band between about 2300 cm$^{-1}$ to about 2400 cm$^{-1}$. An absorption band includes absorption lines at several wavelengths, which means that the absorption is high at particular wavelengths in the band. Examples of particular wavelengths include about 3309 cm$^{-1}$ for detecting $C_2H_2$ and about 2324 cm$^{-1}$ for detecting $CO_2$, though, of course, other wavelengths may be suitable for detecting these gases or other gases.

A variety of radiation sources 18 may be used, including ionizing and non-ionizing radiation sources, which may emit coherent radiation. The source 18 may emit radiation having wavelength in a range from near infra-red to mid infrared region. Suitable examples may include thermal radiation sources, LED sources, MEMS sources, and incandescent lamps. In one embodiment, the radiation source 18 is a laser source. A laser source is monochromatic, and provides a narrow wavelength band sometimes referred to as a coherent electromagnetic field. In some instances, a tunable diode laser (TDL) may be used as it can be tuned or set to produce radiation at individual wavelengths to detect and monitor several gases individually in the fluid. In addition, the TDL can also be set to produce and monitor different absorption lines for the same gas for confirmation and accuracy. In some instances, a quantum cascade laser (QCL) can be used as the source due to its ability to produce radiation of wavelengths in the mid IR range, and due to its tunable nature and its narrow linewidth, which can be used to monitor the hyperfine lines in the gas spectrum.

Figure 2A:
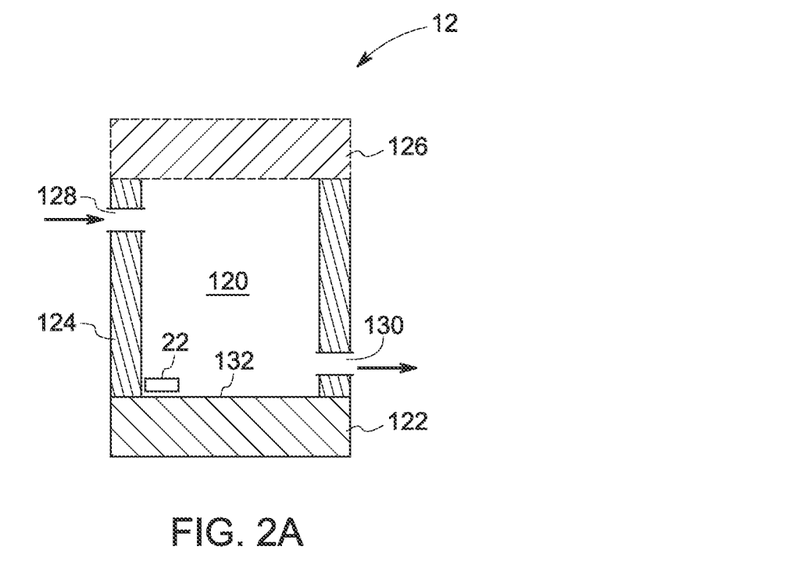
FIGS. 2A-2D are schematics of various designs of a fluid container, in accordance with some embodiments of the invention.

The device 10 further includes a temperature sensor 22 for monitoring the temperature of the sample fluid 14 contained in the container 12. In some specific embodiment, the temperature sensor 22 is located in the container 12 as shown in FIG. 2A. The temperature sensor 22 may be an electrical sensor or an optical sensor. In some specific embodiments, the temperature sensor 22 is a linear temperature sensor. Suitable examples of the electrical temperature sensor 22 may include thermocouples, resistive temperature detectors (for example Pt100, Pt1000), thermistors, semiconductor sensors or diodes. Some example of optical temperature sensing techniques may include surface plasmon resonance (SPR), and interferometry. Criteria and tradeoffs for selecting a sensor type or types from among the available options for a given situation will be apparent to those skilled in the art.

In some embodiments, when the sample fluid 14 is substantially transparent to radiation 20, the radiation 20 may or may not be absorbed depending on the presence or absence of the selected gas in the sample fluid 14. In the instances when a gas is present in the sample fluid 14, the selected gas absorbs the corresponding wavelength radiation, and raises its temperature on absorption of the radiation energy. Consequently, the sample fluid 14 gets heated up due to the heat transfer from the gas to the fluid. The corresponding change in temperature of the sample fluid 14 is measured by the temperature sensor 22. In some other embodiments, in absence of a selected gas, there is no absorption of the corresponding radiation 20, and consequently no change in temperature of the sample fluid 14 is observed.

In some other embodiments, the sample fluid 14 itself may absorb a substantial portion of the radiation 20, and a corresponding change in the temperature of the sample fluid 14 may be observed. In these instances, the change in temperature ($\Delta T_F$) of the sample fluid 14 is measured relative to the change in temperature ($\Delta T_{RF}$) of a reference fluid, as discussed previously. In the presence of gas in the sample fluid 14, the change in temperature ($\Delta T_F$) of the sample fluid 14 may be measurably higher than the change in temperature ($\Delta T_{RF}$) of the reference fluid.

As discussed above, a change in temperature of the sample fluid 14 (or a relative change in temperature of the sample fluid 14 with respect to the reference fluid) may be observed if a gas is present in the sample fluid 14 corresponding to the radiation directed to the fluid 14. The range of the temperature change of the sample fluid 14 may depend on various parameters, for example the composition and concentration of the selected gas, the wavelength of radiation, path length, and power of the radiation source. For example, when a laser source of power 30 mW irradiates a fluid containing 1 ppm of acetylene gas with radiation of wavelength 3300 cm$^{-1}$ and path length of about 5 mm, the expected change in temperature is about 60 micro kelvin. In another example, for a fluid containing 1 ppm of carbon dioxide, the expected change in temperature is about 800 micro-kelvin.

Resolution of the temperature sensor may vary case by case. In some embodiments, the temperature sensor of high resolution, for example 20 micro kelvin may be desirable. In some embodiments, the temperature sensor of lower resolution may be sufficient for the temperature measurement. For example, in case of carbon dioxide, for 1 ppm sensitivity, a temperature sensor of resolution 200 micro kelvin may be used. In some embodiments, the temperature sensor 22 may have resolution between about 20 micro kelvin and about 10 kelvin. One skilled in art knows to use a suitably sensitive temperature sensor according to the expected range of the change in temperature of the fluid for a particular gas.

The sensitivity of the temperature change measurement depends on the magnitude of the temperature change signal, which may generally be adversely affected by heat losses through conduction, convection, and radiation. Thus, it may be desirable to design the fluid container 12 to reduce heat losses and thereby increase the temperature rise signal of the temperature sensor. It may also be desirable to have a small measurement time (that is, time spent in taking the temperature change measurement), which can be attained by reducing the thermal mass of the container.

FIGS. 2A-2D illustrate various possible designs for the container 12. The illustrative container 12 is cylindrical in shape, and has a volume space 120 defined by a bottom wall 122 and side walls 124. The container 12 may further have an optional top wall 126. The container 12 is configured to contain the fluid or a sample of the fluid 14. The sample fluid 14 may be poured into the container 12 or may be received in the container 12 from the equipment (for example, transformer) by connecting the container 12 to the equipment. In some embodiments, the container 12 may have an inlet 128 and an outlet 130 to receive and discharge the fluid.

In one embodiment, the length "L" of the volume space 120 may be in a range from about 1 mm to about 10 mm. A greater pathlength may increase the absorption of the radiation by the dissolved gas and the fluid. In one embodiment, an internal dimension of the of the volume space 120 may be in a range from about 1 mm to about 10 mm.

Furthermore, the thickness of the walls of the container 12 in part determines sensitivity of the measurement. By changing the thickness of the container walls, heat losses may be reduced to promote generation of a more sensitive temperature rise signal. In one embodiment, the thickness of the bottom wall 122 may be in between about 0.1 mm to about 10 mm. The thickness of the top wall 126 may be in a range from about 0.1 mm to about 10 mm. The side wall 124 may have thickness in the range from about 0.5 mm to about 10 mm.

With respect to material, a thermally insulative material may be used to form the container walls. A thermally insulative material may reduce heat transfer through conduction. As used herein, a thermally insulative material may also be referred to as low thermal conductivity material having thermal conductivity less than about 10 W/(m-K). Suitable examples of such material may include, but are not limited to, glass, calcium fluoride ($CaF_2$), and polytetrafluoroethylene (Teflon). Other examples include a non-porous polymer material. In some other embodiments, the container walls may be made of a thin metal interior wall, and covered by the thermally insulative material.

Figure 2B:
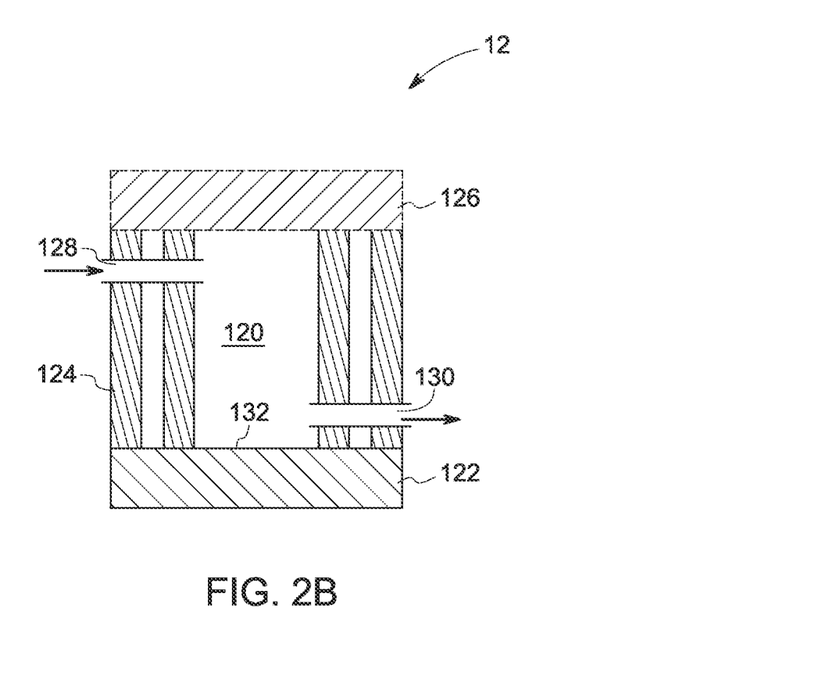

In addition, several other arrangements may be made to the container 12 to reduce the heat losses. Typically, heat is transferred through container walls by conduction, and heat further escapes from an outer surface of the container wall through convection and radiation. A convection loss through side walls 124 may be minimized by reducing the surface area of the side wall 124. In some embodiments, the side wall 124 may have a double wall having air or vacuum within the double wall to increase the conduction resistance as illustrated in FIG. 2B.

In some embodiments, the top wall 126 of the container 12 may have an open region to allow radiation to enter the container 12. In some embodiments, the top wall 126 may have a transparent region (for example, a window) to allow desired wavelengths to pass through. The transparent window may be made of an IR/MID IR transparent material with low thermal conductivity, for example ZnSe, $CaF_2$, or $MgF_2$. Such a transparent window can be placed at any suitable wall of the container 12 to allow radiation to enter the volume space 120.

Figure 2C:
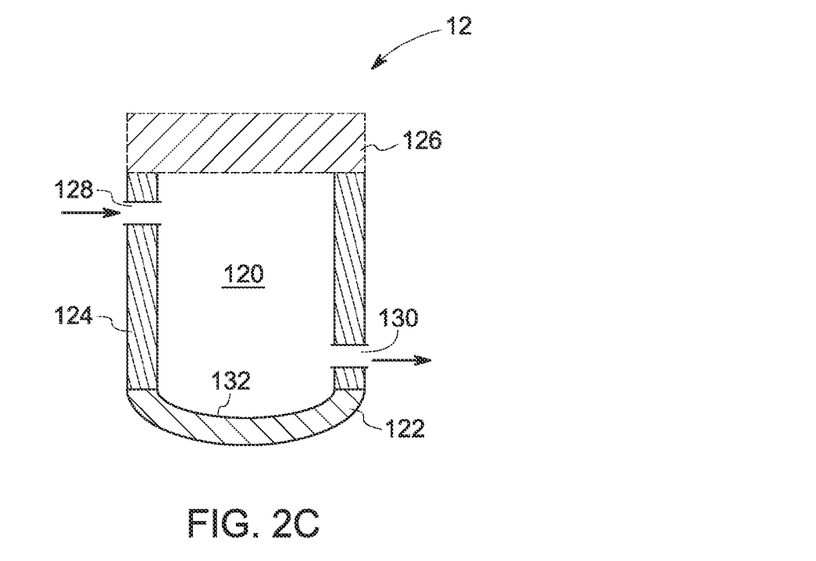
Figure 2D:
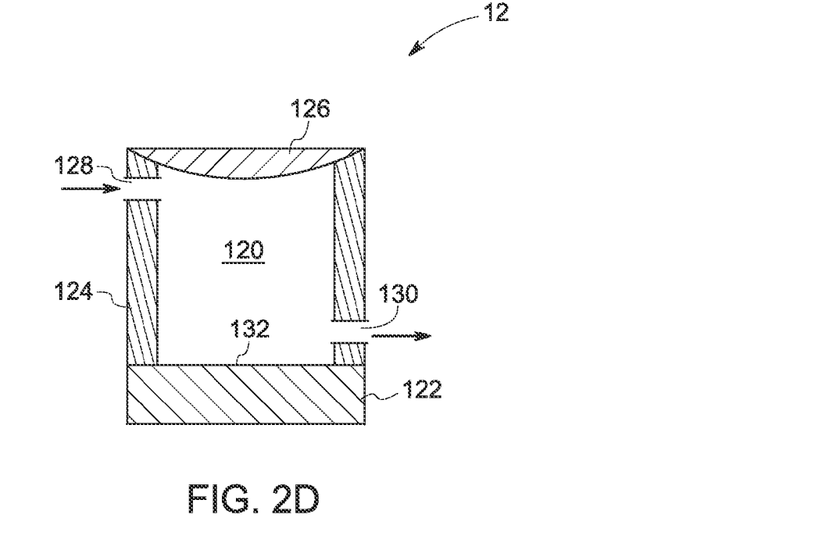

In one embodiment, at least the top wall 126 or the bottom wall 122 are made of a thermally insulative and transparent material. The top transparent wall may allow radiation to enter the volume space, and the transparent bottom wall may allow radiation to pass through to avoid any heating by excess radiation. In some instances, an inner surface 132 of the bottom wall 122 may be polished to redirect or reflect the radiation back to pass through the top end. FIG. 2C illustrates some embodiments where the bottom wall 122 may be shaped as curved/parabolic. In some specific embodiments, the bottom wall 122 may be a parabolic reflector. In some embodiments as illustrated in FIG. 2D, the top wall 120 may be in the shape of a lens to focus the radiation to a region of the volume space (for example, the center of the container 12) to avoid absorption of radiation by the side walls, and to avoid any absorption by the temperature sensor placed inside the container 12.

For further reduction of conduction losses, the container 12 may be placed on an insulating surface, for example glass wool, fiber glass, foam, or wood. In some instances, the container 12 may also be suspended in air or vacuum with the help of a support or wires. A low pressure vacuum (for example, less than about 0.1 bar) may help to reduce the convection losses.

Thus, as discussed above, a change in temperature of the sample fluid 14 (or a relative change in temperature of the sample fluid 14 with respect to the reference fluid) corresponding to radiation of a particular wavelength indicates the composition of the gas present in the sample fluid 14. Furthermore, it may be desirable to calculate the amount of the dissolved gas or gases in the sample fluid 14. The concentration of a gas in the sample fluid 14 is a function of the change in temperature ($\Delta T_E$) of the sample fluid 14 (or a relative change in temperature ($\Delta T_F - \Delta T_{RF}$) of the sample fluid 14 with respect to the reference fluid) due to absorbed energy by the gas, and may be calculated consequently. That is, the magnitude of the change in temperature may further be a measure of the concentration of the gas in the sample fluid 14.

Referring again to FIG. 1, the device 10 further includes a data analyzer 24 coupled to the temperature sensor 22. The data analyzer 24 receives an output signal from the temperature sensor 22, which signal is a function of the concentration of the gas in the sample fluid 14. The data analyzer 24 uses an algorithm to determine the concentration of the gas, as discussed and given below in formulas (i) and (ii).

If radiation of a particular wavelength and intensity $I_0$ is incident on a fluid, and the fluid is transparent to the radiation, then the power absorbed due to a gas present in the fluid is given by $-I_0(1-e^{-\alpha cL})$ where $\alpha$ is the absorptivity of the gas at the incident wavelength, c is the gas concentration, and L is the path length. "Path length" refers to an interaction length between the electromagnetic source and the fluid. The fluid is usually irradiated for a time period, and the temperature of the fluid increases with time until attaining a steady state temperature. The steady-state temperature rise can then be given by $$(\Delta T_F)_{ss} = I_0(1-e^{-\alpha cL})R_{th} \quad \text{formula (I)}$$

where $R_{th}$ is the effective thermal resistance between the device and the environment.

Therefore, by measuring $(\Delta T_F)_{ss}$, the concentration of the gas, "c," can be calculated. The calculation involves knowledge of $R_{th}$ which can either be pre-determined or the device can be pre-calibrated.

For very low gas concentrations, i.e. $\alpha cL \ll 1$, $$e^{-\alpha cL} \sim 1 - \alpha cL$$

$$\text{thus}, (\Delta T_F)_{ss} = I_0 \alpha cL R_{th} \quad \text{formula (ii)}$$

If the fluid is not fully transparent to the radiation at the incident wavelength, then there will be a temperature rise $(\Delta T_{RF})_{SS}$ due to absorption by the fluid. In such a case, $$(\Delta T_F)_{ss} - (\Delta T_{RF})_{SS} = I_0 e^{-\beta}(1-e^{-\alpha cL})R_{th} \quad \text{formula (iii)}$$

Where $\beta$ is the absorption coefficient of the fluid.

The rate of change of temperature may also be used to calculate the gas concentration 'c'. Initially, when the radiation is not incident, the $\Delta T_F$ is zero. Once the radiation source is turned on, the $\Delta T_F$ starts to increase as a function of time (t). The equation describing this rise is given by $$\Delta T_F = (\Delta T_F)_{SS}(1-e^{-t/\tau})$$

Where $\tau$ is the thermal time constant of the system and is given by $R_{th}C$ where C is the heat capacity of the system. (If the fluid also absorbs a part of the radiation, $\Delta T_F$ should be replaced by $\Delta T_F - \Delta T_{RF}$).

The rate of change of temperature rise is thus given by $$\frac{d(\Delta T_F)}{dt} = \frac{I_0}{C}(1 - e^{-\alpha cL})e^{-t/\tau}$$

from which the gas concentration can be determined. Once again, if c is small, the equation can be written as $$\frac{d(\Delta T_F)}{dt} = \frac{I_0}{C}(\alpha cL)e^{-t/\tau}$$

Thus the rate of change of temperature rise is proportional to the gas concentration. This method can be used to determine the concentration without waiting for steady state to be reached.

The algorithm is programmed in such a way to automatically determine the concentration of the selected gas, based on calculations employing the above formulas.

The data analyzer 24 can calculate the concentration of the gas corresponding to the change in temperature ($\Delta T_F$) of the sample fluid 14 (or a relative change in temperature ($\Delta T_F - \Delta T_{RF}$)) observed in the presence of the gas based on the formulae provided above. The algorithm may further involve predetermined data for the change in temperature $\Delta T_{RF}$ of the reference fluid corresponding to particular wavelengths of radiation.

Individual measurements can be made for several gases at predetermined wavelengths. Moreover, multiple readings can be taken for a number of fluid samples from different locations of the equipment to confirm the compositions and concentrations of the gases in the equipment.

The disclosed device and method provide a direct (in-situ) approach for monitoring dissolved gases in a fluid without extracting gases from the fluid unlike known methods and devices. The method and device selectively determine individual gases and their concentrations in the fluid, for example in dielectric oils used in transformers. The device is small and compact, and thus is suitable for use on-site. In other words, the device is field deployable, and can be employed near a system such as transformer for periodic gas detection analysis.

Figure 3:
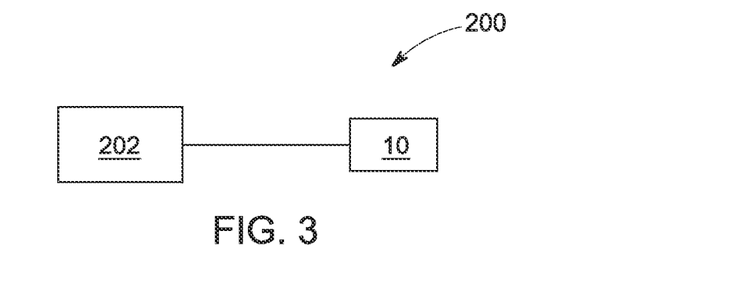
FIG. 3 is a schematic view of a system, in accordance with an embodiment of the invention.

In some embodiments, a system 200 is provided that includes a transformer 202 in fluid communication with the device 10, as discussed above, for analyzing dissolved gases in the transformer oil, as illustrated in FIG. 3. The device 10 may be connected to the transformer 202 periodically for the analysis. In some instances, the device 10 may be permanently in connection with the transformer 202 to take the measurements, and analyze the dissolved gases in the oil. Measurements may be made at a predetermined interval or upon demand.

EXAMPLES

The example that follows is merely illustrative, and should not be construed to be any sort of limitation on the scope of the claimed invention.

Example 1

The following example demonstrates a change in temperature of a fluid on absorption of radiation of a wavelength.

Figure 4:
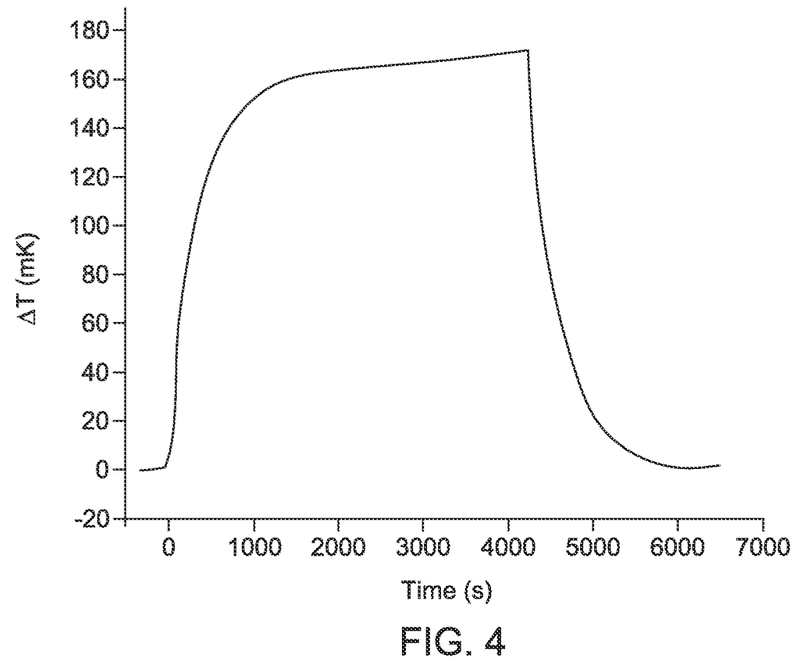
FIG. 4 is graph showing a temperature change of a fluid in response to a radiation, in accordance with one embodiment of the invention.
Figure 5:
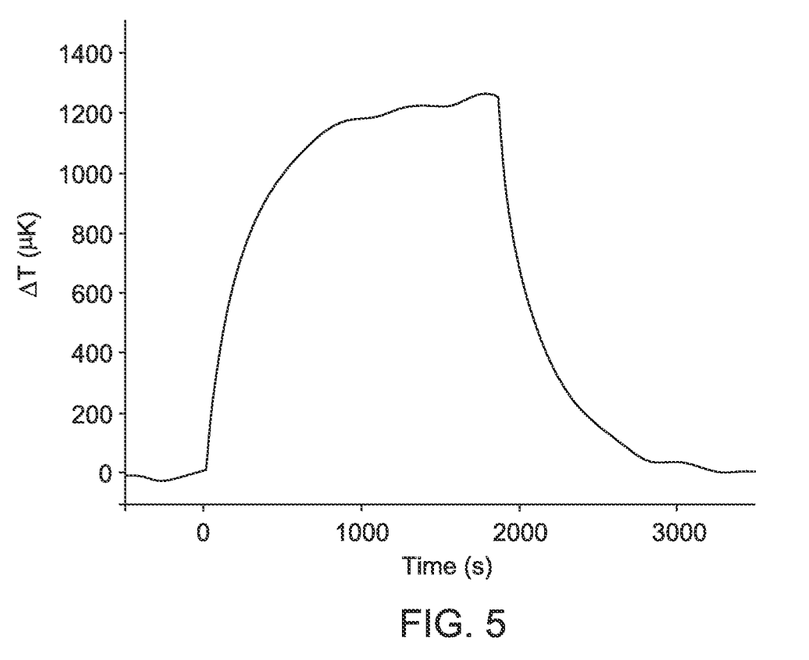
FIG. 5 is graph showing a temperature change of a fluid in response to a radiation, in accordance with another embodiment of the invention.

Two samples, a water sample and a transformer oil sample were taken in small amounts (about 300 microliters) in individual containers. Both samples did not contain any gas. The samples were irradiated individually with radiation of wavelengths about 1942 nm and about 1947 nm, respectively, by using a quantum cascade laser (QCL). Each sample was measured for a change in temperature through a resistive temperature sensor (Pt100). FIGS. 4 and 5 are graphs showing the changes in temperatures of the water sample and the oil sample as a function of time during a period until the temperature of the samples reached a steady state temperature. The change in temperature ($\Delta T_{ss}$) was measure about 170 millikelvin for the water sample, and about 1.2 millikelvin for the oil sample. The change in temperature for each of the samples confirms measurable absorption of the radiation by the samples.

It is clear from the above examples that a change in temperature of a fluid is observed corresponding to an absorption of radiation of a particular wavelength. If a gas were present in the fluid, a higher change in the temperature of the fluid would be observed, assuming the gas absorbed the particular wavelength of radiation, used to make the measurement.

Example 2

The following example demonstrates initial calculations to estimate approximate temperature rise for a gas dissolved in the dielectric oil.

Figure 6:
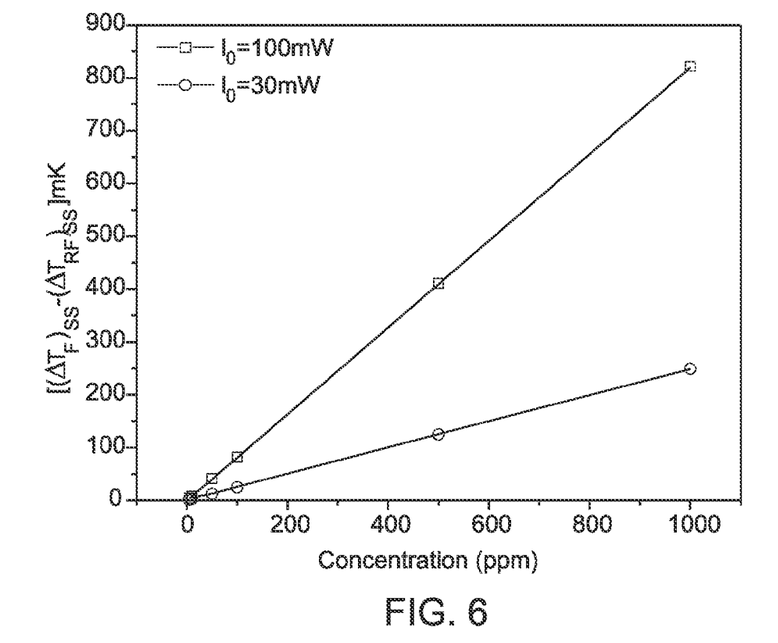
FIG. 6 is graph showing a temperature change of a fluid with respect to concentrations of a gas dissolved in the fluid, in accordance with one embodiment of the invention.
Figure 7:
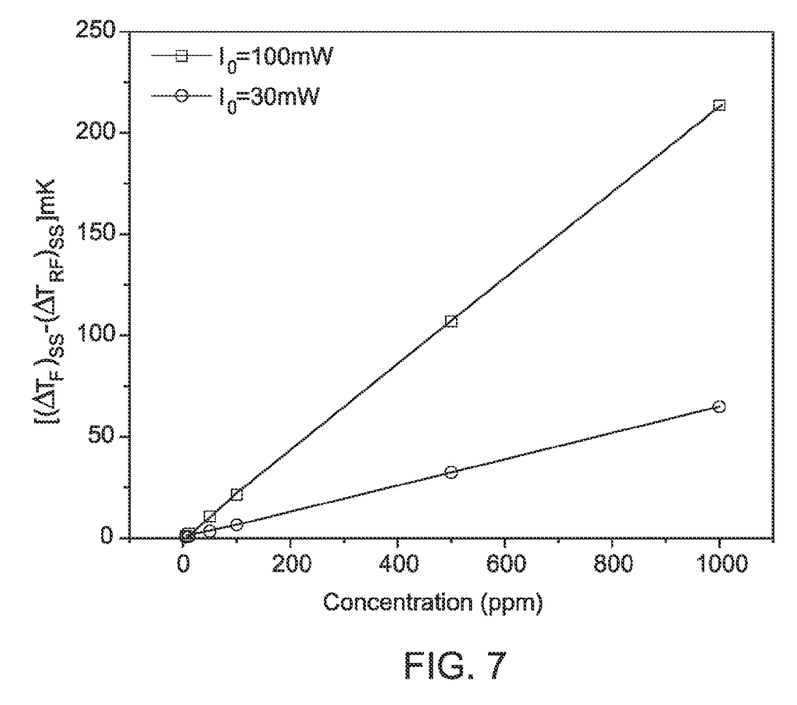
FIG. 7 is graph showing a temperature change of a fluid with respect to concentrations of a gas dissolved in the fluid, in accordance with another embodiment of the invention.
Figure 8:
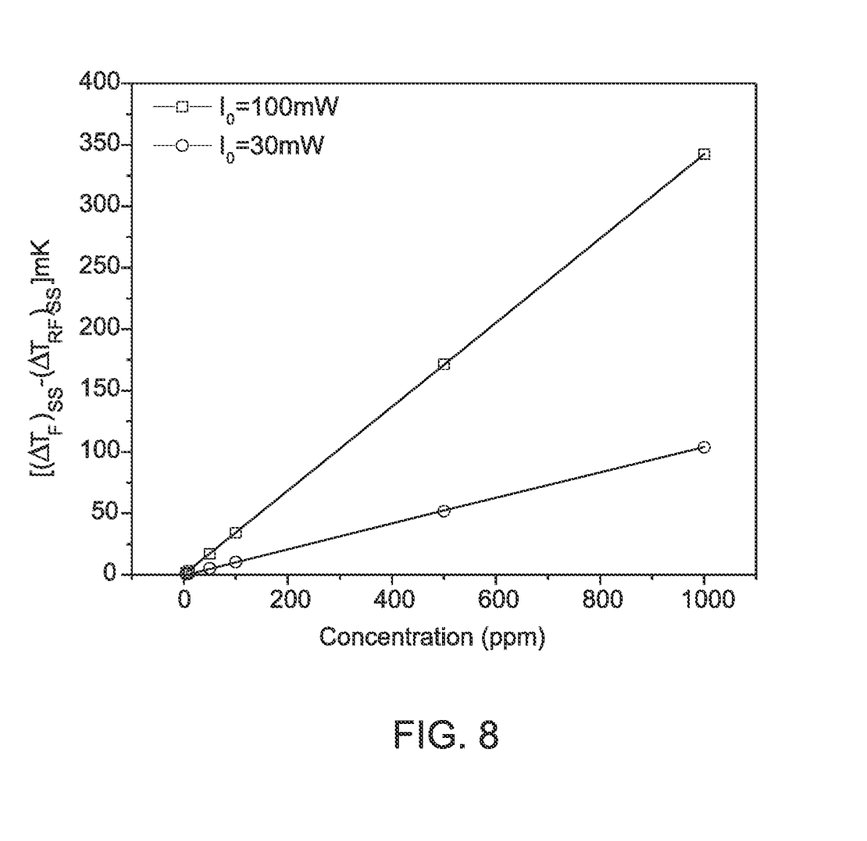
FIG. 8 is graph showing a temperature change of a fluid with respect to concentrations of a gas dissolved in the fluid, in accordance with yet another embodiment of the invention.

3 samples of transformer oil were considered for these calculations. Table 1 shows 3 samples, each containing a dissolved gas, the amount of the gas present in the sample, and the wavelength used to irradiate the sample. A fluid container as shown in FIG. 2A, made of quartz, having volume space length of 5 millimeters and diameter of 3 millimeters was considered to be filled with a sample. For calculations, the wall thicknesses of the container were not considered, and heat losses from the container were lumped into a thermal resistance of about 700 k/W. The expected temperature change for different gases and for different gas concentrations were calculated per formula (ii) given above, and are shown in the graphs of FIGS. 6, 7, and 8.

TABLE 1

| Sample | Gas dissolved | Wavelength (cm$^{-1}$) |
| --- | --- | --- |
| Sample 1 | $CO_2$ | 3300 |
| Sample 2 | $C_2H_2$ | 2127 |
| Sample 3 | CO | 2314 |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for detecting and monitoring dissolved gases in a liquid, comprising the steps of:
   receiving a liquid in a container, the liquid containing a dissolved fault gas;
   identifying a wavelength of electromagnetic radiation corresponding to a spectral absorption range of the fault gas;
   irradiating the liquid with electromagnetic radiation having the identified wavelength;
   measuring a temperature change of the liquid in response to the irradiation; and
   determining a concentration of the fault gas in the liquid based on a temperature change of the liquid in response to the irradiation.

2. The method of claim 1, wherein irradiating the liquid with electromagnetic radiation comprises irradiating the liquid with coherent electromagnetic radiation.

3. A device for detecting and monitoring a fault gas dissolved in a liquid, the device comprising:

a liquid container;

an electromagnetic radiation source for directing radiation into the liquid container, the electromagnetic radiation source configured to emit radiation having a wavelength corresponding to a spectral absorption range of a fault gas dissolved in a liquid contained in the liquid container, a temperature sensor for monitoring a temperature of a liquid contained in the liquid container, and a data analyzer for determining concentration of the fault gas in the liquid based on a temperature change of the liquid in response to radiation from the radiation source.

4. The device of claim 3, wherein the liquid container comprises a thermally insulative material.

5. The device of claim 4, wherein the thermally insulative material comprises quartz, calcium fluoride, or polytetrafluoroethylene.

6. The device of claim 3, wherein the liquid container has a volume in a range from about 1 microliter to about 10 milliliters.

7. The device of claim 3, wherein the radiation source emits coherent radiation.

8. The device of claim 7, wherein the radiation source emits coherent radiation at a wavelength in a range from near-infrared to mid-infrared region.

9. The device of claim 3, wherein the electromagnetic radiation source comprises a laser source.

10. The device of claim 9, wherein the laser source comprises a tunable laser.

11. The device of claim 3, wherein the liquid comprises one or more coolants, insulating fluids, mineral oils, vegetable oils, beverages, organic chemical compounds, or combinations of any of these.

12. The device of claim 3, wherein the fault gas comprises one or more gases such as hydrogen, oxygen, nitrogen, carbon monoxide, carbon dioxide, methane, ethane, ethylene, and acetylene.

13. The device of claim 3, wherein the temperature sensor comprises an optical temperature sensor or an electrical temperature sensor.

14. The device of claim 3, wherein the temperature sensor is disposed in the liquid container.

15. A system comprising a transformer containing an insulating oil in fluid communication with a device as defined in claim 3.

* * * * *